United States Patent
Tets et al.

(10) Patent No.: US 10,080,761 B2
(45) Date of Patent: *Sep. 25, 2018

(54) METHOD FOR TREATING RECURRING SKIN AND MUCOUS MEMBRANE DISEASES CAUSED BY HSV-1 AND HSV-2

(71) Applicants: Viktor Veniaminovich Tets, St. Petersburg (RU); Georgy Viktorovich Tets, St. Petersburg (RU)

(72) Inventors: Viktor Veniaminovich Tets, St. Petersburg (RU); Georgy Viktorovich Tets, St. Petersburg (RU); Viktor Iosifovich Krutikov, St. Petersburg (RU)

(73) Assignees: Viktor Veniaminovich Tets, St. Petersburg (RU); Georgy Viktorovich Tets, St. Petersburg (RU)

( * ) Notice: Subject to any disclaimer, the term of this patent is extended or adjusted under 35 U.S.C. 154(b) by 0 days.

This patent is subject to a terminal disclaimer.

(21) Appl. No.: 15/676,716

(22) Filed: Aug. 14, 2017

(65) Prior Publication Data

US 2017/0368081 A1    Dec. 28, 2017

Related U.S. Application Data

(63) Continuation of application No. 14/896,619, filed as application No. PCT/RU2014/000420 on Jun. 6, 2014, now Pat. No. 9,757,396.

(30) Foreign Application Priority Data

Jun. 7, 2013   (RU) ................ 2013127035

(51) Int. Cl.
| | | |
|---|---|---|
| *A61K 31/63* | (2006.01) | |
| *A61K 9/06* | (2006.01) | |
| *A61K 9/00* | (2006.01) | |
| *A61K 9/02* | (2006.01) | |
| *A61K 9/10* | (2006.01) | |

(52) U.S. Cl.
CPC ........... *A61K 31/63* (2013.01); *A61K 9/0014* (2013.01); *A61K 9/0034* (2013.01); *A61K 9/02* (2013.01); *A61K 9/06* (2013.01); *A61K 9/10* (2013.01)

(58) Field of Classification Search
CPC .... A61K 31/63; A61K 9/0014; A61K 9/0031; A61K 9/0034; A61K 9/02; A61K 9/06; A61K 9/10
See application file for complete search history.

(56) References Cited

U.S. PATENT DOCUMENTS

| | | |
|---|---|---|
| 6,417,181 B1 | 7/2002 | Bender et al. |
| 6,569,864 B1 | 5/2003 | Douglas et al. |
| 2003/0086992 A1 | 5/2003 | Tanaka et al. |
| 2004/0157848 A1 | 8/2004 | Maziasz |
| 2005/0037032 A1 | 2/2005 | Catania et al. |
| 2013/0287841 A1 | 10/2013 | Tets et al. |

FOREIGN PATENT DOCUMENTS

| | | |
|---|---|---|
| DE | 3544409 A1 | 10/1986 |
| DE | 10210319 A1 | 9/2003 |
| EP | 1038868 A2 | 9/2000 |
| EP | 1136472 A1 | 9/2001 |
| EP | 2659891 A1 | 11/2013 |
| RU | 1405269 A1 | 12/1993 |
| RU | 2182828 C1 | 5/2002 |
| RU | 2199526 C2 | 2/2003 |
| RU | 2373951 C1 | 11/2009 |
| RU | 2452490 C1 | 6/2012 |
| WO | 2000/034234 A1 | 6/2000 |
| WO | 2012/091610 A1 | 7/2012 |

OTHER PUBLICATIONS

English translation (2014) of RU 2199526 (2003), 6 pages total.
International Preliminary Report on Patentability issued by the International Searching Authority in International Application No. PCT/RU2016/000624, dated Mar. 20, 2018.
International Search Report issued by the International Searching Authority in International Application No. PCT/RU2016/000624, dated Mar. 6, 2017.
Stahl, P.H. et al., "Pharmaceutical Salts: Properties, Selection, and Use" John Wiley & Sons (2002) p. 331.
Rothaus, C., "Genital Herpes" NEJM Resident 360 (Aug. 18, 2016) (retrieved from <https://resident360.nejm.org/content_items/genital-herpes> on Jun. 24, 2017), 3 pages total.
Written Opinion issued by the International Searching Authority in International Application No. PCT/RU2016/000624, dated Mar. 6, 2017.
Berge, S. M., et al., "Pharmaceutical Salts", Journal of Pharmaceutical Sciences (Jan. 1977), vol. 66, No. 1, pp. 1-19.

(Continued)

*Primary Examiner* — Savitha M Rao
(74) *Attorney, Agent, or Firm* — Troutman Sanders LLP

(57) ABSTRACT

The invention relates to medicine and specifically to methods for treating recurring forms of diseases related to the family of herpes viruses. A method for treating recurring diseases of the skin and mucous membranes caused by HSV-1 and HSV-2 involves applying a preparation to an affected area, said preparation including a base containing 0.5% or 1% of an active substance, namely a (2,6-dichlorophenyl)amide salt of carbopentoxysulfanilic acid of general formula (I): where X is Na, K, $NH_4$; the preparation is applied twice daily for 3-5 days and, should prodromes appear, a second course of treatment is carried out, in which the preparation is applied 1-2 times daily for 2-3 days; the base containing the active substance can be in the form of a cream, an ointment, a gel, a suspension, suppositories, a patch or a film. Carrying out the second course of treatment provides a sharp increase in therapeutic efficacy, even to the extent of preventing relapse over a prolonged period of observation as a result of the effect of the preparation, upon reuse, on the viruses persisting in nerve cells.

19 Claims, No Drawings

(56) References Cited

OTHER PUBLICATIONS

Didkovskii et al. "Gerpes—virusnaya infekstiya: Klinicheskoe znachenie i printsipy terapii." Russkii Meditsinskii Zhurnal, 2004, vol. 12, No. 7, pp. 459-464, Retrieved from the Internet: <<URL:http://www.rmj.ru/articles_378.htm>>. Last accessed Dec. 7, 2015.
Extended European Search Report dated Dec. 10, 2013 issued in corresponding European Patent Application No. 11853372.8.
Furman, P. A. et al, "Acyclovir-Resistant mutants of Herpes Simplex Virus Type 1 Express Altered DNA Polymerase or Reduced Acyclovir Phosphorylating Activities", Journal of Virology (Dec. 1981), vol. 40, No. 3, pp. 936-941.
International Preliminary Report on Patentability, issued in corresponding PCT International Application No. PCT/RU2011/000060 and English Translation Thereof.
International Search Report and Written Opinion dated Sep. 25, 2014, issued in corresponding International Application No. PCT/RU2014/000420 and English Translation thereof.
International Search Report and Written Opinion dated Sep. 29, 2011, issued in corresponding International Application No. PCT/RU2011/000060 and English Translation Thereof.
International Preliminary Report on Patentability Issued in International Application No. PCT/RU2014/000420 dated Oct. 12, 2015 and English Translation Thereof, 9 pages.
Mashkovskiy, Lekarstvenniye Sredstva, Moscow, 2001, vol. 2, pp. 321-334.
Noueiry, A. O., et al., "Identification of Novel Small-Molecule Inhibitors of West Nile Virus Infection", Journal of Virology (Nov. 2007), vol. 81, No. 21, pp. 11992-12004.
Supplemental/Extended European Search Report Issued in European Patent Application No. 14806838.0 dated Jan. 13, 2017, 9 pages.

METHOD FOR TREATING RECURRING SKIN AND MUCOUS MEMBRANE DISEASES CAUSED BY HSV-1 AND HSV-2

CROSS-REFERENCE TO RELATED APPLICATIONS

This application is a continuation of U.S. patent application Ser. No. 14/896,619, filed on Dec. 7, 2015, which is the U.S. National Stage of International Patent Application No. PCT/RU2014/000420, filed on Jun. 6, 2014, which published as International Publication No. WO 2014/196901 A1 on Dec. 11, 2014, and which claims the benefit of Russian Patent Application No. 2013127035, filed on Jun. 7, 2013. The contents of the foregoing applications are hereby incorporated by reference in their entirety.

TECHNICAL FIELD

The invention relates to medicine and specifically to methods for treating recurring forms of diseases related to the family of herpes viruses.

BACKGROUND ART

Treatment of viral infections is an extremely serious problem in the modern medicine. Most viral infections are either immune to antiviral therapy or very difficult to treat due to low effectiveness of existing preparations as well as rapid variability of causative agents, which results in the emergence of resistant forms thereof.

A known method for treating diseases caused by herpes virus consists in using a pharmaceutical composition that contains a known substance—1,3-diethylbenzimidazole triiodide—as an active substance, see RU 2420281 C2.

In practice this method has very little effect, the majority of herpes virus strains are resistant towards the active component contained in the composition used in the method, which is not a specific antiviral substance.

Another known method for preventing and treating a chronic and frequently recurring herpes virus infection uses antiviral preparations and immune system correctors; during remission period a synthetic gamma-D-glutamyl-L-tryptophan dipeptide is used intranasally in the amount of 50-100 μg daily for 7-10 days, and during exacerbation period a synthetic gamma-D-glutamyl-L-tryptophan dipeptide is used intranasally in the amount of 100 μg daily for 10 days along with an antiviral therapy using Valaciclovir preparation in the amount of 500 mg orally, 1 pill twice daily for 5-10 days, and also using Penciclovir preparation for external use—applying it to affected areas 3-4 times daily for 5-7 days, see RU 2373951 C1.

The applicants of the abovementioned method believe that it helps shorten the acute period and prolong the remission period of herpes virus infection thanks to normalization of the amount of T helper cells, suppressor T cells, NK cells and relative proportions thereof, as well as the increase in formation of endogenic interferon gamma.

Since antiviral activity of Valaciclovir is low due to developed resistance of herpes viruses towards this preparation, the method has low effectiveness and its effect results only from nonspecific factors, namely, its stimulating action on the immune system.

The aforesaid also applies to the method for treating infections caused by HSV-1 and HSV-2, CMV, EBV, which is based on administering an antiviral preparation and recombinant human interferon-Alpha 2; the antiviral preparation is embodied as Valaciclovir in the amount of 500 mg orally, 1 pill twice daily for 5-10 days, and the human interferon-Alpha 2 is administered in the amount of 3 min IU by diluting it in 5 or 10 ml of saline solution and injecting into each nostril 3 drops twice daily for 10 days, then 2 drops for 10 days and 1 drop for 10 days, see RU 2391981 C2.

Another known method for treating herpes virus infections comprises conducting major autohemotherapy (MAHT) in the dosage of 3-9 mg/ml in a single-administration volume of 200-240 ml until exacerbation symptoms appear, whereupon antiviral preparations are additionally administered while continuing the MAHT, see RU 2178669 C1.

The effectiveness of this method is primarily determined by the effectiveness of the antiviral preparations; as for the ozone therapy, its contribution to the effectiveness of treatment of herpes virus diseases is not proven. It should also be noted that such treatment of blood is quite unsafe and can cause a series of grave and harsh side effects.

Another known method for treating a chronic recurring herpes virus infection by administering antiviral preparations together with immune system correctors and topical preparations is characterized in that the antiviral preparation is embodied as Valtrex in the amount of 1 pill of 500 mg twice daily for 5-10 days, the immune system corrector is embodied as Polyoxidonium in the amount of 6 mg once daily every other day in the form of 10 intramuscular injections, and the interferon inducer is embodied as Neovir in the amount of 2.0 ml injected intramuscularly once daily every other day and as Derinat, which is used locally for applications as 0.25% solution 3 times daily during 20 min for 5 days; after completing the course of relapse treatment a course of Cycloferon is prescribed in the amount of 2.0 ml injected intramuscularly on day 1-, 2-, 4-, 6-, 8-, 11-, 14-, 17-, 20- and 23, together with Aciclovir in the amount of 400 mg twice daily for 10 days, B group vitamins—Berocca in the amount of 1 pill once daily for 1 month, after which Alpisarin is used in the amount of 2 pills twice daily for 10 days, followed by 10-day pause, and then the Alpisarin treatment is repeated in the amount of 2 pills twice daily for 10 days, combining it with a biostimulant—Moskoviya balm in the amount of 35 drops 3 times daily for a month, see RU 2197969 C1.

This method is very complicated and involves a lot of medical preparations and other non-medicinal substances, as well as injections and applications.

Each component used in the method has its own contraindications and side effects, and using these components in a complex combination has not been sufficiently studied. Low effectiveness of this method is mainly due to low effectiveness of specific antiviral preparations Valtrex and Aciclovir.

Although there exist many methods that are described as being effective for treating diseases caused by herpes viruses, reducing the number of relapses so far has been possible only by implementing methods of treatment that employ enteral forms of existing antiherpetic preparations, most of all Aciclovir [Rooney J F, Straus S E, Mannix M L, Wohlenberg C R, Alling D W, Dumois J A, Notkins A L Oral acyclovir to suppress frequently recurrent herpes labialis. A double-blind, placebo-controlled trial. Ann Intern Med. 1993; 118: 268-272].

However, such treatment takes a lot of time and, most importantly, enteral administration of such preparations often results in serious side effects and complications.

Another known method uses parenteral forms of preparations, in particular, a known method for treating diseases of the skin and mucous membranes caused by HSV-1 and HSV-2 involves applying to an affected area a cream or an ointment containing (2,6-dichlorophenyl)amide salt of carbopentoxysulfanilic acid of general formula:

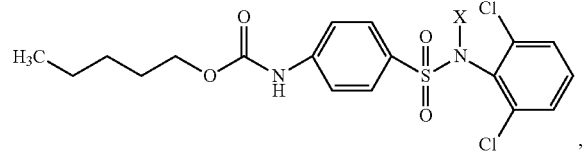

This method is described in RU 2452490 C1, page 5: "The inventive substance can be contained . . . in ointments, creams or other forms that can be applied to skin and mucous membranes . . . ".

This method has been taken as a prototype of the present invention. Implementation of this method does not cause such serious side effects as with treatment methods that employ enteral forms of preparations.

However, RU 2452490 C1 describes a treatment of diseases caused by herpes viruses that involves only one course.

The disadvantage of the prototype method described in RU 2452490 C1 consists in that it does not provide an effective treatment of recurring forms of diseases.

SUMMARY OF THE INVENTION

It is an object of the present invention to increase the effectiveness of treatment of recurring forms of diseases of skin and mucous membranes caused by HSV-1 and HSV-2 by means of the substance described in RU 2452490 C1.

According to the invention, in the method for treating recurring diseases of the skin and mucous membranes caused by HSV-1 and HSV-2 by applying a preparation to an affected area, said preparation includes a base containing 0.5% or 1% of an active substance, namely a (2,6-dichlorophenyl)amide salt of carbopentoxysulfanilic acid of general formula:

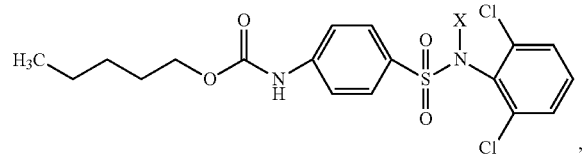

where X is Na, K, $NH_4$
the preparation is applied twice daily for 3-5 days and, should prodromes appear, a second course of treatment is carried out, in which the preparation is applied 1-2 times daily for 2-3 days. The base containing the active substance can be in the form of a cream, an ointment, a gel, a suspension, suppositories, a patch or a film.

The applicant has not found any sources of information containing data on the features of the invention, namely the second application of preparation to the affected area, said preparation including a base containing the active substance—(2,6-dichlorophenyl)amide salt of carbopentoxysulfanilic acid of general formula:

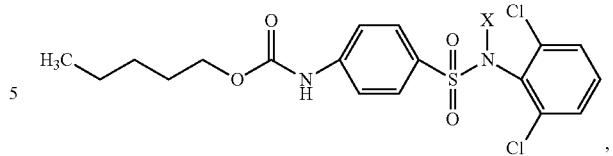

which enables to conclude that the inventive method conforms to the patentability criterion "Novelty" (N).

It is a known fact that during a relapse the herpes antiviral therapy can be implemented as a second course of the same antiviral preparation, but with implementation of known methods such treatment proves to have little effect, not only due to the emergence of resistant forms of the virus after the first course of treatment, but also because known methods ensure inhibition of viruses only in the epithelial cells and do not affect viruses in neurons, where the viruses persist even after multiple applications. However, medicobiological studies conducted by the department of microbiology, virology and immunology of Pavlov State Medical University of St. Petersburg have demonstrated that the implementation of the features of the claimed method results in the inhibition of viruses not only in epithelial cells but also, surprisingly, after a second course of treatment the viruses are inhibited in neurons too. Therefore specifically after the second course of therapy an important technical result is achieved, which consists in the inhibition of viruses in neurons and, correspondingly, an effective, often radical, treatment of recurring forms of diseases or at least a significant prolongation of the remission period (usually by several times). It should be noted that the inhibition of herpes viruses that persist in nerve cells only takes place during second courses that involve administration of the active substance in accordance with the inventive method, whereas other methods that involve second courses of application of other antiviral preparations to skin and mucous membranes have no significant effect whatsoever on viruses in nerve cells.

Although the treatment of various diseases using second courses is well known, there are no sources that contain data on the inhibition of viruses persisting in nerve tissue after the second course of treatment, which in applicant's opinion enables to conclude that the claimed method conforms to the patentability criterion "Inventive Step" (IS).

BRIEF DESCRIPTION OF THE DRAWINGS

The invention is further explained by way of detailed description of examples of its embodiments, without reference to any drawings.

PREFERRED EMBODIMENT

The implementation of the claimed method is further explained by means of the examples provided below.

Example 1. Treatment of a Herpes Relapse

Clinical progression of a recurring form of HSV-1 or HSV-2 infection is characterized by various properties—age of illness, duration of relapses, location of herpetic eruptions, area of damage, reaction of regional lymph nodes, addition of a secondary infection and effectiveness of the previously conducted antiviral therapy; however, the key criterion is the frequency of relapses. Light form of the infection—up to 4 relapses per year, medium—5-7 relapses per year, severe—8 or more relapses per year. Existing topical preparations can reduce the intensity and duration of a relapse, but have no effect on the frequency of relapses.

5 patients with medium form of the disease (5-7 relapses per year) and 5 patients with severe form (8 or more relapses per year) were chosen for the study. All patients had many years of experience of treatment with Aciclovir in the form of cream and pills. The previously used preparations did not reduce the number of relapses for any of the patients. The study did not include patients that had more than 25% of cases of "false" prodromal symptoms or had non-progressing subsequent elements of damage (which stopped at the papule stage). During each relapse all patients applied to the affected area a cream based on lanolin containing 0.5% of the active substance—(2,6-dichlorophenyl)amide sodium salt of carbopentoxysulfanilic acid—twice daily in the mornings and evenings. The duration of treatment was 4-5 days.

Pain syndrome disappeared after 24-48 hours. Within the same period the swelling subsided and the appearance of new eruptions stopped. After 36-72 hours the healing and epithelization process began. No cases of a form resistant towards the treatment were observed.

During the observation all patients were instructed to use the cream upon the appearance of the first prodromes (sensations of pain) that manifest before the first eruptions.

The second course of treatment lasted for 2-3 days, no eruptions appeared and the unpleasant sensations were gone within 24 hours. Two patients used another second course when eruptions appeared. The duration of treatment was 3 days.

In six patients with a recurring form of the herpetic infection an unexpected change of the course of the infection was observed. The chronic infection lost its recurring nature—for a prolonged period of observation (2 years) no signs of a relapse were observed; for other patients the duration of remission increased significantly, averaging 1 year 5.5 months.

Example 2. Treatment of an Extensive Form of Herpes

Studies were conducted on 12 patients with an extensive form of herpes virus characterized by simultaneous emergence of several focal lesions. During a relapse all patients applied to the affected area the preparation in the form of an ointment containing 1% of the active substance twice daily in the mornings and evenings. The duration of treatment was 3-4 days.

Pain syndrome disappeared after 24-48 hours. Within the same period the swelling subsided and the appearance of new eruptions stopped. After 36-72 hours the healing and epithelization process began.

Upon signs of a relapse (on average, after 4-5 months) a second course of treatment was conducted during 2-3 days. After 2 years of observation 5 patients had no relapses, for other patients the average duration of remission was 14 months.

Example 3. Treatment of an Extensive Form of Herpes with Added Secondary Bacterial Infection Studies were conducted on 9 patients with an extensive form of herpes virus characterized by the addition of a secondary bacterial infection at the areas of skin damage. During a relapse all patients applied to the affected area the preparation in the form of a 1% suspension that additionally included a biocidal agent (RU 2422137 C1), twice daily in the mornings and evenings. The duration of treatment was 5 days.

Pain syndrome disappeared after 24-36 hours. Within the same period the swelling subsided and the appearance of new eruptions stopped. After 36-72 hours the healing and epithelization process began. No cases of a form resistant towards the treatment were observed.

All patients had signs of a relapse after an average of 4 months, after which a second course of treatment was conducted for 5 days. After its completion 5 patients had no relapses during the period of observation (2 years), for other patients the average duration of remission was 15 months.

Example 4. Treatment of a Genital Form of Herpes

Studies were conducted on 16 patients with a genital form of herpes (7 men and 9 women).

The method of treatment consisted in that the men applied 0.5% cream to the affected area twice daily in the mornings and evenings, whereas women used vaginal suppositories and cream. The duration of treatment was 3-4 days.

Pain syndrome disappeared after 24-36 hours. Within the same period the swelling subsided and the appearance of new eruptions stopped. No cases of a form resistant towards the treatment were observed.

Signs of a relapse appeared after an average of 4-5 months. A second course of treatment was conducted for 4 days. After that 6 men has no signs of a relapse during the period of observation (2 years), for one man the duration of remission was 1.5 years. After 2 years of observation 2 women had no relapses, for 7 women the average duration of remission was 12 months.

Implementation of the method can combine the preparation with interferon inducers as well as other antiherpetic preparations and/or antimicrobial agents.

Thus, conducting a second course of treatment according to the present invention provides a sharp increase in therapeutic efficacy, even to the extent of preventing relapse over a prolonged period of observation (possibly, a complete recovery) as a result of the effect of the preparation, upon reuse, on the viruses persisting in nerve cells; whereas second courses of treatment according to other methods have no such effect, the effectiveness of treatment during second courses is reduced because of emerging resistant forms, and the duration of remission is usually shortened.

INDUSTRIAL APPLICABILITY

The invention can be implemented by means of known materials and equipment. In applicant's opinion, this enables to conclude that the invention conforms to the criterion "Industrial Applicability" (IA).

The invention claimed is:

1. A method for treating recurring diseases caused by a herpes virus in a subject in need thereof, said method comprising administering to the subject a first agent which is (2,6-dichlorophenyl)amide salt of carbopentoxysulfanilic acid of the general formula:

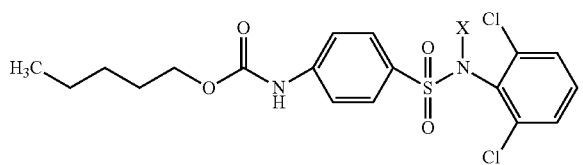

wherein X is Na, K, or NH4, and a second agent, which is interferon or an antiviral agent.

2. The method of claim 1, wherein said second agent is selected from the group consisting of Interferon, Valaciclovir, Penciclovir, Aciclovir, and Valtrex (valacyclovir hydrochloride).

3. The method of claim 1, wherein said second agent is an antiviral agent.

4. The method of claim 3, wherein said antiviral agent is Valaciclovir, Penciclovir, or Aciclovir.

5. The method of claim 1, wherein said second agent is interferon.

6. The method of claim 1, wherein X is Na.

7. The method of claim 1, wherein X is K.

8. The method of claim 1, wherein X is $NH_4$.

9. The method of claim 1, wherein the herpes virus is herpes simplex virus type 1 (HSV-1).

10. The method of claim 1, wherein the herpes virus is herpes simplex virus type 2 (HSV-2).

11. The method of claim 1, wherein the first agent is administered as a preparation selected from the group consisting of a cream, an ointment, a gel, a suspension, a suppository, a patch, and a film.

12. The method of claim 1, wherein the first active agent is administered as a preparation comprising 0.5% or 1% of the (2,6-dichlorophenyl)amide salt of carbopentoxysulfanilic acid.

13. The method of claim 1, wherein the first active agent is administered to the affected skin or mucous membranes.

14. The method of claim 1, comprising a second period of administration of the first agent upon symptom recurrence after a first period of administration.

15. The method of claim 14, wherein the first period of administration of the first agent is twice daily for 3-5 days, and the second period of administration of the first agent is 1-2 times daily for 2-5 days.

16. A method for treating a disease caused by a herpes virus in a subject in need thereof, said method comprising administering to said subject a pharmaceutical composition comprising a (2,6-dichlorophenyl)amide salt of carbopentoxysulfanilic acid of the general formula:

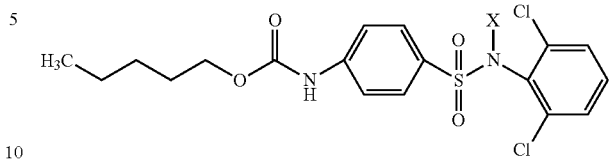

wherein X is Na, K, or $NH_4$, and a second agent which is interferon or an antiviral agent,
wherein said pharmaceutical composition is administered in an amount effective for treating a herpes virus infection.

17. The method of claim 16, wherein said second agent is Valaciclovir, Penciclovir, or Aciclovir.

18. A method for treating a disease caused by a herpes virus in a subject in need thereof, said method comprising administering to said subject a pharmaceutical dosage form comprising a (2,6-dichlorophenyl)amide salt of carbopentoxysulfanilic acid of general formula:

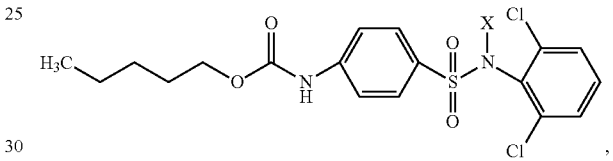

wherein X is Na, K, or $NH_4$, and a second agent which is interferon or an antiviral agent, wherein said salt and said second agent are present in the dosage form in an amount effective for treating a herpes virus infection.

19. The method of claim 18, wherein said second agent is Valaciclovir, Penciclovir, or Aciclovir.

* * * * *